(12) United States Patent
Lai

(10) Patent No.: US 6,256,369 B1
(45) Date of Patent: Jul. 3, 2001

(54) COMPUTERIZED TOMOGRAPHY SCANNER WITH LONGITUDINAL FLYING FOCAL SPOT

(75) Inventor: Ching-Ming Lai, Wakefield, MA (US)

(73) Assignee: Analogic Corporation, Peabody, MA (US)

(*) Notice: Subject to any disclaimer, the term of this patent is extended or adjusted under 35 U.S.C. 154(b) by 0 days.

(21) Appl. No.: 09/282,674

(22) Filed: Mar. 31, 1999

(51) Int. Cl.⁷ .................................................. G01N 23/00
(52) U.S. Cl. .................................................. 378/14; 378/9
(58) Field of Search ........................ 378/4, 9, 10, 11, 378/14, 15, 19, 20

(56) References Cited

U.S. PATENT DOCUMENTS

| | | | |
|---|---|---|---|
| 5,550,886 | 8/1996 | Dobbs et al. | 378/19 |
| 5,625,661 * | 4/1997 | Oikawa | 378/15 |
| 5,841,829 | 11/1998 | Dolazza et al. | 378/4 |

* cited by examiner

Primary Examiner—David P. Porta
(74) Attorney, Agent, or Firm—McDermott, Will & Emery

(57) ABSTRACT

In an improved computerized tomography scanner, the X-ray source is configured to have a focal spot that is variable in position in a direction parallel to or substantially parallel to the longitudinal or rotation axis of the scanner. Data are sampled from two different focal spot positions displaced in the longitudinal direction as the gantry rotates through successive projection angles, thereby providing two fan beams at different longitudinal positions. The data may be sampled at a detector array having a single or multiple rows. In this manner, at least two slices are scanned contemporaneously, and thus the scan throughput rate is at least doubled. The invention is further applicable to a system utilizing multiple detector rows.

35 Claims, 7 Drawing Sheets

COMPUTERIZED TOMOGRAPHY SCANNER WITH LONGITUDINAL FLYING FOCAL SPOT

BACKGROUND OF THE INVENTION

In a third-generation computerized tomography (CT) scanner, an X-ray source and a detector array are mounted to a disk assembly, which is rotatable about an object to be scanned. The rotating disk assembly is supported by a rigid, stationary gantry. The detector array comprises a plurality of channels extending laterally from a central channel. During a scan, the source and detectors scan the object at incremental rotation angles. A process referred to as reconstruction generates a series of two-dimensional images, or slices, of the object from the captured data.

FIG. 1 is an axial or front view of a third-generation X-ray CT scanner, including an X-ray source 20 and a detector array 22 mounted on a disk assembly rotatable about an object at an angular velocity of ω. The detector array 22 is typically disposed as a row in the shape of a circular arc, and centered about a point 26, referred to as the "focal spot", where X-ray radiation emanates from the X-ray source 20. The X-ray beam emanating from the focal spot and incident on the detector array therefore define a fan beam. A rotating coordinate system x'y'z', fixed relative to the disk assembly, is used in FIG. 1 and subsequent figures to illustrate the position of the focal spot of the X-ray source 20 with respect to the detector array 22. The z' axis coincides with the z axis of a stationary coordinate system (x,y,z). The x'y' plane is coplanar with the xy plane, and rotates about the z' axis at angular velocity ω. The source 20 and the detector array 22 lie on the x'y' plane, and the y' axis intersects the rotation center or isocenter 24 and the center channel 22A of the detector array. In a conventional fixed focal spot system, the focal spot position remains fixed on the y' axis throughout a scan.

For the purpose of discussion, the direction on the x'y' plane, i.e. within the rotation plane of the fan beam, parallel to, or substantially parallel to, the x' axis, is referred to herein as the "lateral" direction, and the direction parallel to, or substantially parallel to, the z' axis is referred to as the "longitudinal" direction.

It is well understood that oscillatory movement of the focal spot in the x'y' plane during a scan can improve the image-quality of a CT scanner, as described, for example, in U.S. Pat. No. 5,841,829, incorporated herein by reference. This is referred to as a "flying focal spot". In this configuration, the focal spot 26 is made to oscillate in a lateral direction, between positions a and b, as shown in FIG. 1. The displacement of the focal spot in the lateral direction, parallel to the x' axis is plotted with respect to time in FIG. 2 for a standard case of simple harmonic oscillation of the lateral movement.

During a scan, X-ray intensity is sensed at each detector channel over a range of rotation or view angles, as the disk assembly rotates at an angular velocity ω, and while the X-ray source continuously irradiates the object being scanned. All detector signals are typically sampled at the same time at each rotation angle. The signal of the X-ray intensity incident on a detector is integrated or filtered over a short time duration. During this time duration, focal spot displacement varies slightly near the peak of the sinusoidal oscillation. The lateral positions a and b indicated in FIGS. 1 and 2 represent the mean displacements following the signal integration or filtration.

Oscillating focal spot displacement in the lateral direction, parallel to the x' axis, is equivalent to a tangential offset of the detector array. Usually, the flying focal spot is operated to have displacements a and b located at the equivalent of positive and negative quarter-detector offsets. Under these conditions, the data collected from the focal spot at position a are shifted by a half detector width with respect to the data collected from the focal spot at position b.

By alternating the focal spot between displacement positions a and b at successive rotation angles, the effective number of detectors is doubled. At alternate even and odd rotating angle increments, the data are sampled at the even and odd detection positions respectively, resulting in data that are interleaved in the sampling space. As a result, the spatial resolution of the reconstructed image is doubled. The flying focal spot is applicable to both step-and-shoot scanning and helical scanning.

SUMMARY OF THE INVENTION

In the present invention, the focal spot is made to oscillate in the longitudinal direction, in other words, along a direction parallel or substantially parallel to the z' or the scanner rotation axis. In this manner, an improvement in scan throughput rate is achieved.

In a first aspect, the present invention is directed to an apparatus for and method of computed tomography (CT) scanning. The apparatus of the present invention comprises a CT scanner including an energy source having a focal spot and a detector array for imaging of an object at successive incremental rotation angles about a longitudinal axis. The focal spot has a variable position along a longitudinally directed path during a scan of an object.

In a preferred embodiment, the focal spot moves along a predefined path including a set of multiple positions displaced from one another in a longitudinal direction at each successive rotation angle. The longitudinal movement of the focal spot is preferably in accordance with a oscillatory waveform function selected from the group consisting of square, trapezoidal, and sinusoidal waveform functions.

The focal spot may oscillate between first and second peak amplitude positions in accordance with a sinusoidal waveform function. In this case, the detected signals may be acquired over a short time duration when the focal spot is substantially at each of the first and second peak amplitude positions.

The energy source preferably comprises an X-ray source, and the detector array may comprise a single-row (or more generally a single set of arrayed detectors), or a dual-row detector array (or more generally two sets of arrayed detectors). A collimator may be included for collimating the radiation emitted by the energy source focal spot.

In an embodiment where the focal spot is made to oscillate between first and second positions along a path in the longitudinal direction, the collimator may further comprise: first and second apertures corresponding with the first and second positions, and a baffle, made for example as an extrusion, configured to prevent radiation emitted from a focal spot at the first position from entering the second aperture, and to prevent radiation emitted from a focal spot at the second position from entering the first aperture.

The focal spot may be configured to vary in position along a lateral direction, within one or more of the planes of rotation of the focal spot.

The focal spot may oscillate between first and second positions in the longitudinal direction generating first and second fan beams respectively centered about first and second fan beam planes. In this configuration, the first and second fan beam planes are preferably substantially parallel and are incident at the detector array at first and second longitudinal positions. The detector array may comprise a dual-row detector array having first and second detector subarrays wherein the first fan beam plane is incident at the first detector subarray and wherein the second fan beam plane is incident at the second detector subarray.

Alternatively, the first and second fan beam planes may be tilted so as to (a) converge and intersect before reaching the detector array so that they are diverging when they intersect with the detector array, (b) converge and intersect beyond the detector array, or (c) converge and intersect directly or nearly directly at the detector array.

As mentioned, the detector array may comprise a detector array having first and second detector subarrays, wherein the first fan beam plane is incident at the first detector subarray, and wherein the second fan beam plane is incident at the second detector subarray. The focal spot further generates third and fourth fan beams centered about third and fourth fan beam planes, wherein the third fan-beam plane originates at the first focal post position and is incident at the second detector subarray, and wherein the fourth fan beam plane originates at the second focal spot position and is incident at the first detector subarray. The data acquired for the first, second and a combination of the third and fourth beams can create three slices through the object.

In another aspect, the present invention further includes a focal spot drift compensation mechanism. The mechanism includes a focal spot monitor for monitoring the position of the focal spot during said scan. An averaging unit determines the average position of the focal spot over a time period, based on the monitored positions. A compensation unit compares the average position with a predetermined optimal position, and modifying the focal spot position based on the comparison.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENT

Figure 1:
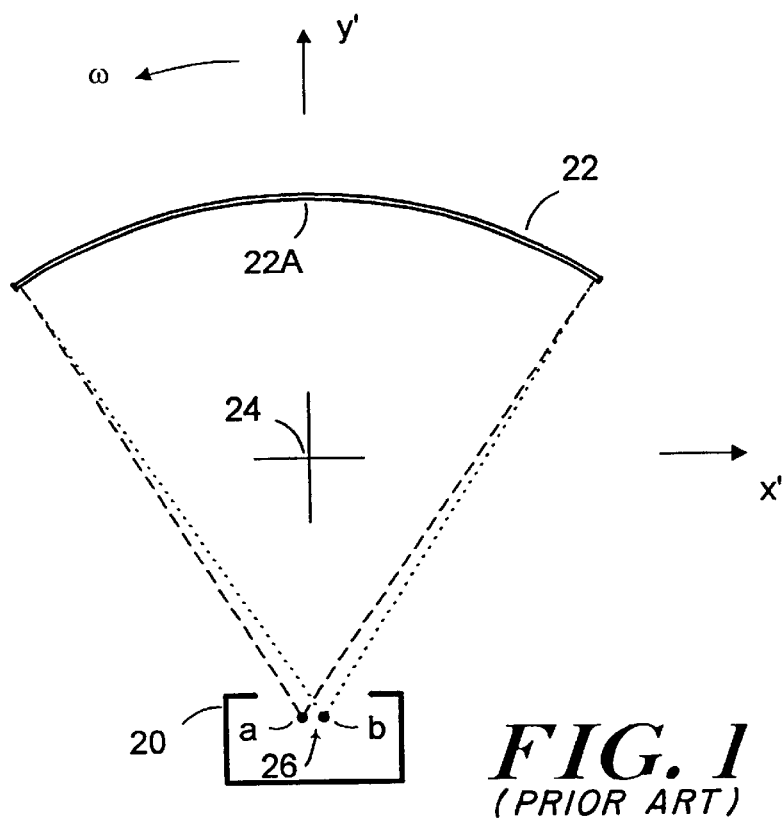
FIG. 1 is a axial or front schematic view of an X-ray CT scanner, including an X-ray source and a detector array mounted on a disk assembly rotatable about an object at an angular velocity of ω, illustrating a conventional flying focal spot oscillating in a lateral direction within the plane of rotation of the focal spot.
Figure 2:
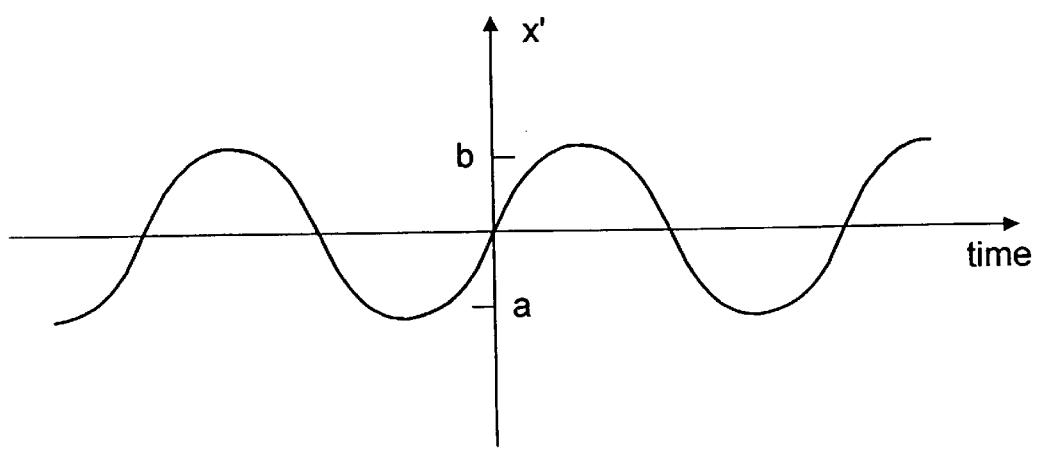
FIG. 2 is a sinusoidal waveform illustrating the magnitude of the mean displacements, a and b, for the lateral flying focal spot illustrated in FIG. 1.
Figure 3:
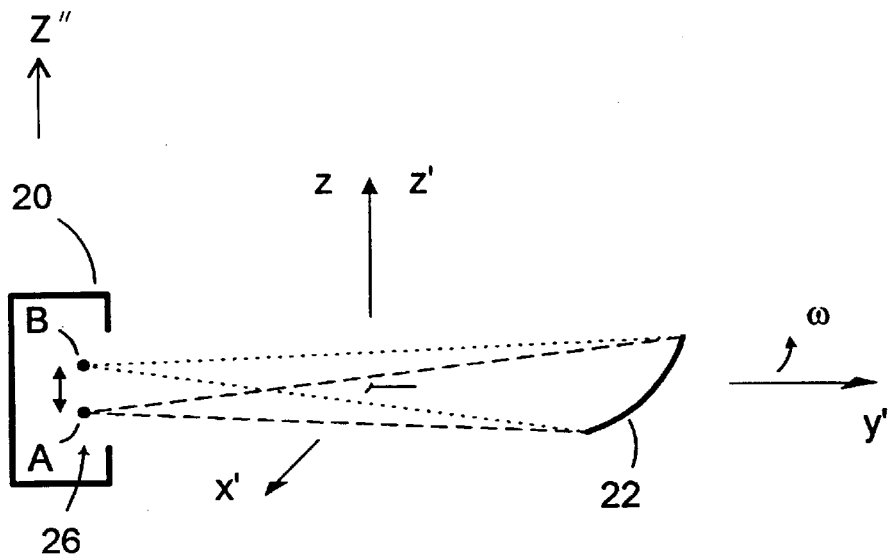
FIG. 3 is a perspective schematic view of a CT scanner system employing a longitudinally-oscillating flying focal spot, in accordance with the present invention.
Figure 4:
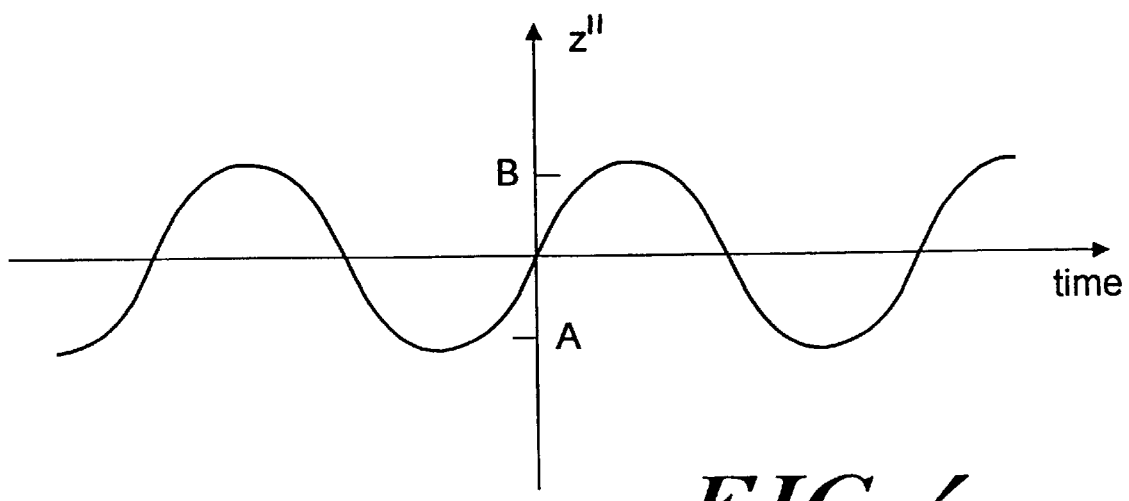
FIG. 4 is a sinusoidal waveform illustrating the position of the flying focal spot as it moves in the longitudinal direction, in accordance with the present invention.

FIG. 3 is a perspective schematic view of one embodiment of a CT scanner system employing a longitudinally-oscillating flying focal spot, in accordance with the present invention. In this configuration, the focal spot 26 is made to oscillate between two positions displaced from one another in the longitudinal direction, for example along the z" axis, between positions A and B, as the source 20 and detector array 22 rotate at a constant angular velocity ω about the z' axis. The sampling sequence and the oscillation period of the focal spot are preferably the same as those of the conventional lateral flying focal spot techniques. However, unlike the conventional techniques, the total longitudinal displacement of the focal spot between positions A and B, shown graphically in FIG. 4, may be varied according to the imaging slice width and other factors, as described below.

By alternating the focal spot between longitudinal positions A and B, the data are effectively sampled in two different z axis positions respectively using two different fan beams. The position oscillation period preferably corresponds with the time between successive projection angle increments for each of the fan beams so that one projection view is taken with each beam during each oscillation period. Thus, if each angular increment between successive projection angles where the focal spot is in position A is 0.25°, the angular increment between projection angles where the focal spot is in position B will also be 0.25°, but preferably displaced from the projection angles where the focal spot is in the position A by 0.125°. Although this requires the data collectors to operate twice as fast (assuming a fixed rotation speed of the rotating gantry), such operation speeds are readily achievable in contemporary data acquisition systems.

Figure 5:
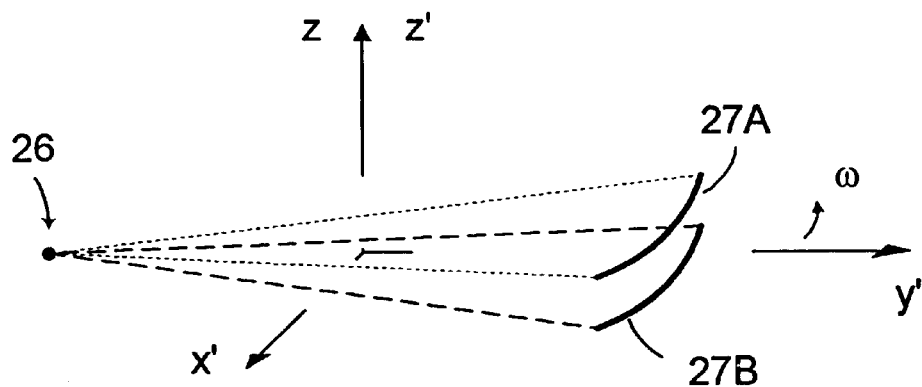
FIG. 5 is a perspective schematic view of a system having two rows of detectors for simultaneous acquisition of data along two slices in a longitudinally-static focal spot system.

The configuration of the present invention is analogous to, but an improvement over a conventional dual-row detector system, having a longitudinally-static or fixed focal spot 26 with two rows of detectors 27A, 27B as shown in FIG. 5.

The longitudinal flying focal spot technique of the present invention is applicable to both step-and-shoot scan and helical scan systems. In a step-and-shoot scan system, data from two object slices are collected contemporaneously, as in the dual-row detector system of FIG. 5. In a helical scan system, the pitch is twice that of the existing single-row detector system. Whether step-and-shoot or helical scan, the longitudinal flying focal spot technique of the present invention doubles the throughput rate of the scanner.

The amplitude of focal-spot displacement between points A and B depends on the distance between the focal spot and the collimator, the aperture of the collimator which defines the thickness of the beam, and the height of the detectors along the z-axis, along with the level of accuracy required for image reconstruction. As a result, there are a number of possibilities for configuring focal-spot displacement and the collimator.

Figure 6:
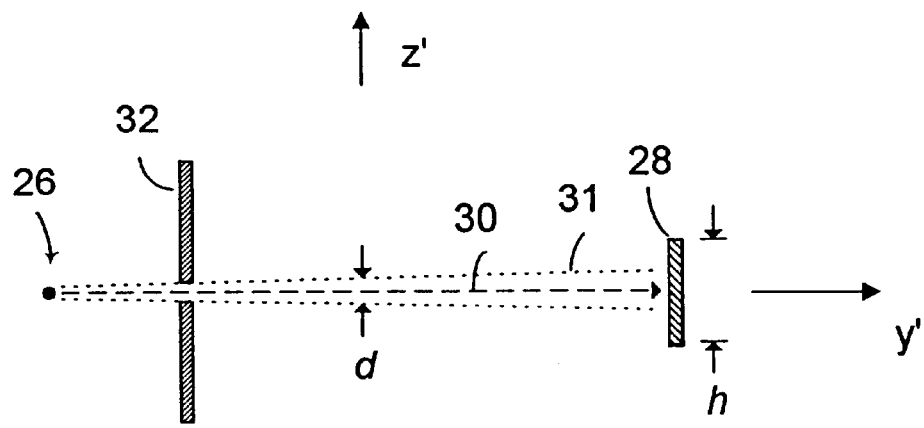
FIG. 6 is a side schematic view of a conventional system having a single row of detectors in a longitudinally-static focal spot system.

First, for the purpose of comparison and illustration, a static or fixed focal spot system with a single row of detectors 28 is considered, as shown in FIG. 6. The central plane 30 of the resulting divergent beam 31, referred to as a "fan beam", is perpendicular to z' axis. The fan-beam 31 diverges from the focal point 26, through the collimator 32, to the detector array 28. The thickness d at the rotation center along the z'-axis is referred to as the slice width. The detector height h accommodates the thickness of the scanning slice at that point, and it is typically 10 to 20 times the lateral distance between two adjacent detectors.

Figure 7:
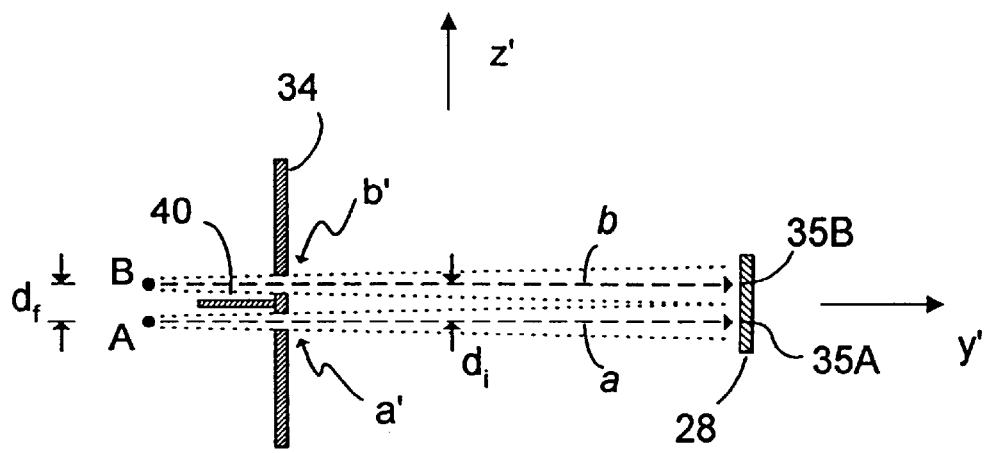
FIG. 7 is a side schematic view of a preferred embodiment of the present invention including a longitudinal flying focal spot in which the two fan-beam planes, a and b, are parallel to each other and normal to the longitudinal axis.

FIG. 7 is a side view of a preferred focal-spot displacement and collimator configuration for the longitudinal flying focal spot system of the present invention. With the double-slit collimator 34, focal spot A defines a fan-beam plane a and focal spot B defines a fan-beam plane b. In this configuration, both fan-beam planes a, b are perpendicular to the z' axis at all projection angles. Image reconstruction for both slices will be as accurate as that for single slice in the conventional system of FIG. 6. The collimator 34 includes double slits a' and b'. The width of each slit defines the thickness of each corresponding fan beam, as in the conventional system. If the distance between the centers of the slits is d, then the distance $d_f$ between focal spots A and B and the interval $d_i$ between the two imaging slices is also d. The incident z-location 35A of fan-beam plane a on the detector array 28 is likewise at the distance d from the incident location 35B of fan-beam plane b.

A baffle 40 cooperates with a collimator 34 so that two slits a' and b' define the two beams mutually exclusive of one another and thus prevent the radiation at focal spot A from passing through slit b' and likewise prevent the radiation at focal spot B from passing through slit a'. It should be evident that the two slits a' and b' can be provided by the baffle 40 and a single slit in the collimator, or alternatively, provided by two slits in the collimator separated by the baffle.

Figure 8:
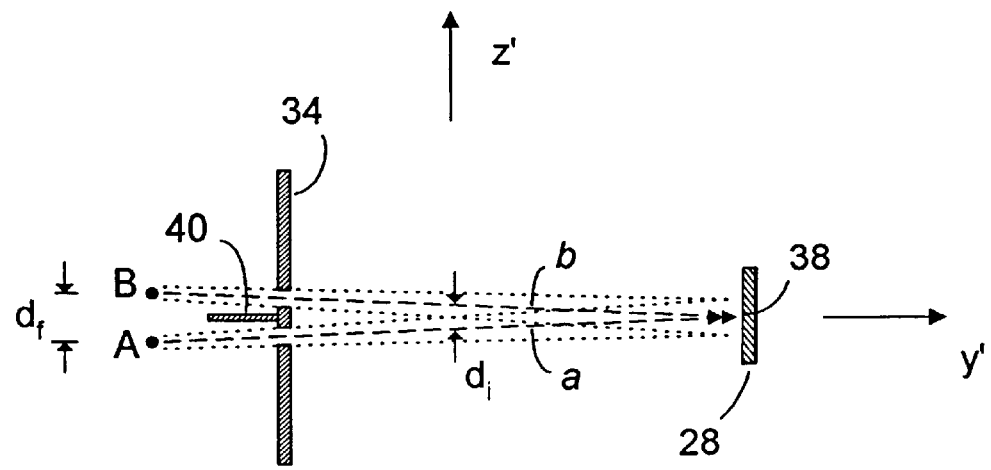
FIG. 8 is a side schematic view of an alternative configuration of the present invention including a double-slit collimator in which the fan-beam planes converge and intersect at the detector array.
Figure 9:
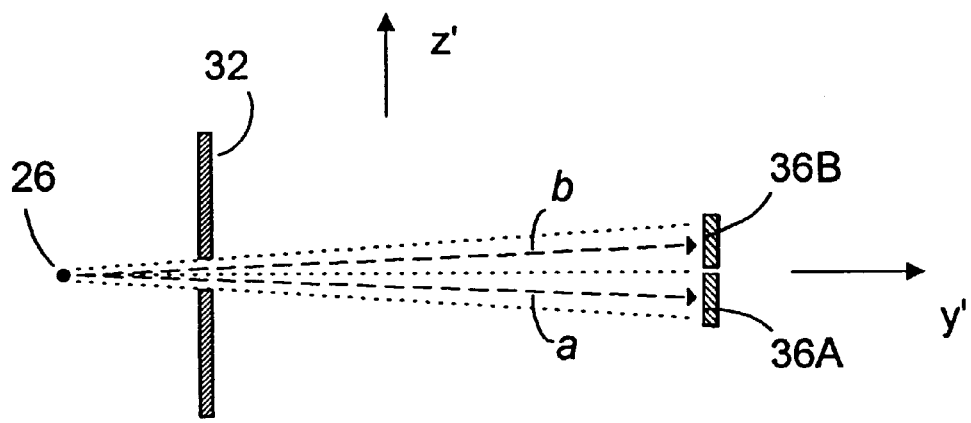
FIG. 9 is a side schematic view of a system having two rows of detectors in a longitudinally-static focal spot system.

In an alternative configuration illustrated in FIG. 8, the incident location 38 of fan-beam plane a at the detector array 28 coincides with that of fan-beam plane b so that the two planes converge and intersect at or near the detector array. The interval $d_i$ between two imaging slices is slightly less than d, and the distance $d_f$ between focal spots A and B is slightly greater than d. In this configuration, both fan beams are of a maximum width allowed by the detector 28 height. However, both fan-beam planes a, b are slightly tilted toward each other, and therefore each does not remain on a constant plane during rotation. This configuration is analogous in operation to a dual-row detector array system as shown in FIG. 9, having a single static or fixed focal point source 26, and dual detector arrays 36A, 36B. It should be noted that for optimal image reconstruction the fan-beam planes a, b (of FIG. 8) should be parallel to the xy-plane at all projection angles. As a result of the tilted fan-beam planes, which rotate about the z axis during a scan, the reconstructed images will not be as accurate as the images derived from the preferred configuration of FIG. 7.

The configurations of FIGS. 7 and 8 illustrate two different cases, one with beams having parallel planes, and the other with beams having non-parallel planes. The FIG. 7 configuration provides ideal parallel fan-beam planes a, b that are perpendicular to the z' axis and are therefore amenable to accurate reconstruction. However, because the planes are parallel and separated by the distance d, the largest slice width detectable by the detector 28 is reduced by d. In contrast, the FIG. 8 configuration allows the slice width to be as large as in the conventional system of FIG. 6, since the planes of both beams are incident at the center of the detector array 38. However, the fan-beam planes a, b are tilted with respect to the z' axis (i.e., non-perpendicular), and therefore will not reconstruct perfectly. Furthermore, the amount of movement of the focal spot $d_f$ in the FIG. 8 configuration is larger than the FIG. 7 configuration, and is therefore more difficult to attain.

Figure 10:
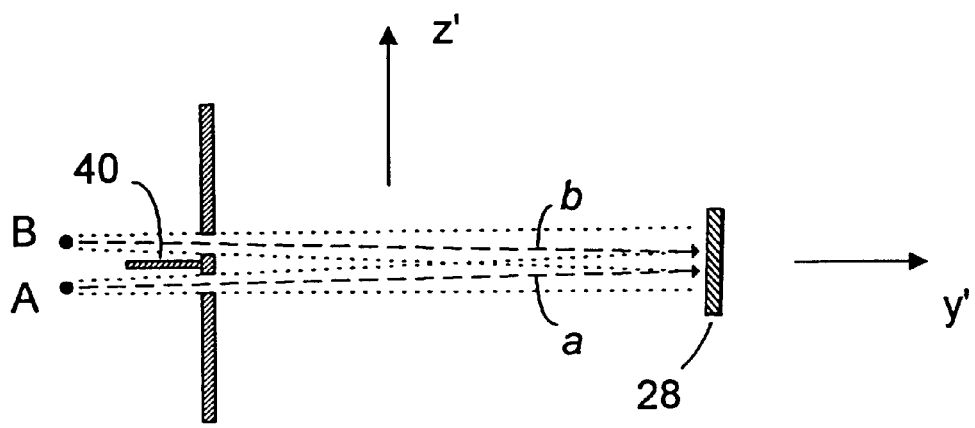
FIG. 10 is a side schematic view of an alternative configuration of the present invention wherein the two fan-beam planes converge and impinge on, but do not intersect at the detector array.

A compromised configuration depicted in FIG. 10 merges the two approaches, with slightly-tilted fan beam planes a, b that converge, but intersect beyond the detector array.

Figure 11:
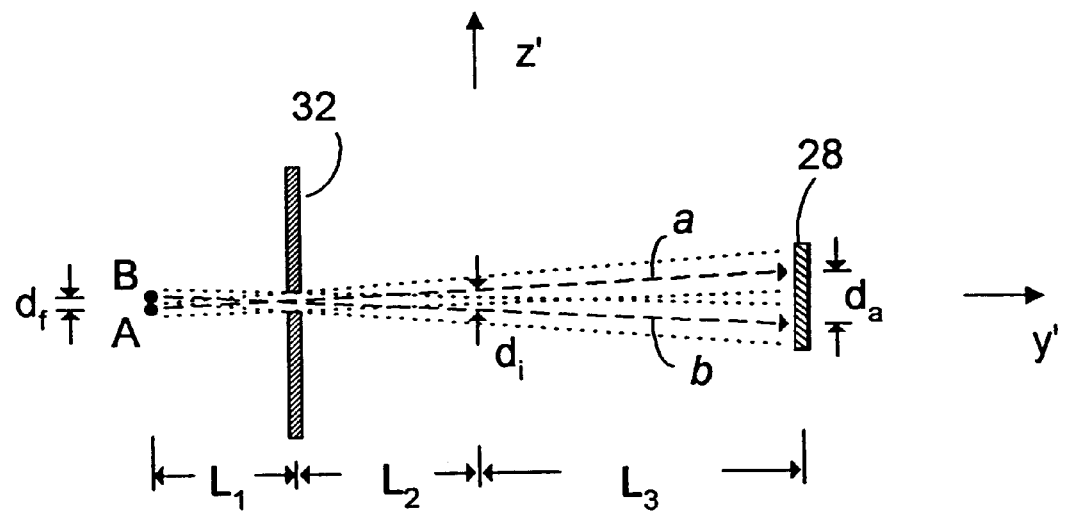
FIG. 11 is a side schematic view of a longitudinal flying focal spot configuration having a single-slit collimator, in which the two fan beam planes have the same longitudinal position, i.e., intersect, at the collimator slit.

An alternative configuration employs a conventional single-slit collimator 32 as shown in FIG. 11. In this configuration, the focal-spot displacement $d_f$ is determined by the interval $d_i$ between the two scanning planes a,b at the rotation center along the z' axis. Assuming $L_1$ to be the distance between the focal spots A, B and the collimator 32, and $L_2$ to be the distance between the collimator 21 and the rotation center, then:

$$d_f = d_i * L_1/L_2. \quad (1)$$

Length $L_2$ is usually greater than $L_1$. Thus, $d_f$ is shorter than $d_i$. This configuration offers the advantage of requiring less displacement $d_f$ between focal spots A, B. A further advantage is that this configuration does not require a baffle as in FIGS. 7, 8, 10, and 12. However, the separation $d_a$ between the two fan-beam planes a, b incident on the detector array 28 is increased to:

$$d_a = d_i * (L_2 + L_3)/L_2 \quad (2)$$

where $L_3$ is the distance from the rotation center (the z' axis) to the detector array 28. Length $L_3$ is comparable with $L_2$, and therefore it follows that distance $d_a$ is about twice that of $d_i$. In comparison to the preferred configuration of FIG. 7, assuming the same detector height, the largest slice width allowable is further reduced. The fan-beam planes a,b are also tilted more than in the other embodiments, and in the embodiment the planes converge and intersect before the detector area, and thus diverge before intersecting the detector array. This embodiment offers the advantages of single collimator operation, and a relatively small amplitude is required for defining the positions of the focal spot, i.e., the focal spot oscillates between two very close positions.

As described above, when the focal spot is made to oscillate in a lateral direction in the x'y' plane, as in the prior art flying focal spot configuration, the result is an interleaving of the data, which doubles spatial resolution of the image. When the focal spot is made to oscillate in the longitudinal direction as proposed by the present invention, data are collected for at least two slices resulting in at least a doubling of the number of slices acquired in a given scan time. A preferred embodiment allows for both lateral and longitudinal oscillation of the focal spot, such that either lateral or longitudinal flying focal spot or both can be used during a scan.

In this latter approach, as illustrated in FIG. 14, where the two approaches are combined, the focal spot moves through four locations with each oscillatory period of the focal spot movement. Assuming (a) the focal spot starts at the position Aa (position A in the longitudinal direction and the position a in the lateral direction) when the focal spot is at a projection angle $\theta_i$ and a projection is taken, (b) the oscillatory movement period is synchronized so that the focal spot returns to the position Aa when the rotates through an angle $\alpha$ to the next projection angle $\theta_{i+1}$, i.e., $\theta_{i+1}-\theta_i=\alpha$, and (c) the rotation of the gantry is at a constant velocity $\omega$, the sequence of positions of the focal spot is preferably as follows:

(1) the focal spot moves from the position Aa to the position Ab at the projection angle $\theta_i+\alpha/4$ where the next projection is taken;

(2) the focal spot is then moved from the position Ab to the position Ba at the projection angle $\theta_i+\alpha/2$ where the next projection is taken;

(3) the focal spot is then moved from the position Ba to the position Bb at the projection angle $\theta_i+3\alpha/4$ where the next projection is taken; and (4) then the focal spot is then moved from the position Bb back to the position Aa at the projection angle $\theta_{i+1}$ where the next projection is taken.

This sequence results in the projections taken with the beam using the focal spot at the longitudinal position A, at alternating lateral positions a and b of the beam at an angular increment of $\alpha/4$ so that the resulting data can be interleaved for that slice. Similarly, the projections taken with the beam using the focal spot at the longitudinal position B are at alternating lateral positions a and b of the beam at an angular increment of $\alpha/4$ (although displaced by angles of $\alpha/2$ from the projection angles of the beam using the focal spot at the longitudinal position A) so that the resulting data can be interleaved for that slice. Thus, data are collected four times during each oscillatory period. Because the rotation is continuous, the data are actually collected at four slightly different rotation angles during each step of rotation, and therefore, data must be collected four times as fast, assuming a constant rotation speed.

Focal spot position in the X-ray tube is determined by the position at which an electron beam strikes the anode target. Oscillation of the focal spot as described above is achieved by deflection of the electron beam by a deflector driven by an oscillating signal. The electron beam can be deflected electrically or magnetically. The electric field plates or magnetic field coils can be installed internal or external to the X-ray tube.

The displacement of the focal spot along the longitudinal direction is in general required to be greater than that of the lateral direction. It is therefore preferred to select a deflection mechanism capable of generating larger displacement amplitude in the longitudinal direction.

Conventional X-ray tubes are designed to operate with a fixed longitudinal position, and therefore the anode target may not have sufficient space in the longitudinal direction for adequate focal spot displacement. The anode target is commonly placed at an incline angle to allow for a wider incident electron beam, and at the same time produce a smaller focal spot as seen in the longitudinal direction. This requires less power to generate X-ray energy for the scan, but requires more power to oscillate the focal spot in the longitudinal direction. In addition, the aperture at the X-ray exit window of a typical X-ray tube may be too narrow to allow for the required longitudinal displacement. Therefore, many existing X-ray tubes are not suitable for implementing the longitudinal flying focal spot by simply adding a longitudinal deflection mechanism.

The X-ray tube can be easily designed to accommodate the required longitudinal oscillation. In the preferred embodiment of FIG. 7, for example, the maximum displacement of the focal spot from the central position may be no greater than 5 mm. The anode target can simply be made larger to accommodate the required deflection amplitude. The anode can be shaped or configured (such as making the incline angle of a rotating anode) so as to oscillate the focal spot in the longitudinal direction more efficiently. The aperture at the X-ray exit window can also be expanded. Internal deflection mechanisms can be employed to enhance deflection efficiency. The tube can also be designed to allow for closer mounting of the external deflection mechanism, to produce more efficient deflection of the electron beam.

In general, the required amplitude for adequate longitudinal oscillation is greater than that for lateral oscillation. If the device is more amenable to focal spot deflection along the lateral direction, then it is preferable to rotate the X-ray tube 90° from the conventional installation. In this 90°-rotated installation, the conventional lateral deflection is used to generate longitudinal displacement, while the added longitudinal deflection is used to generate lateral displacement of the focal spot. In this manner, the more straightforward deflection is operated at a larger amplitude, and the more difficult deflection operates at a smaller amplitude. The complexity and power required in both deflections are therefore more balanced. This configuration is especially attractive for fixed-anode X-ray tubes which do not have to compensate for the gyroscopic torque exerted on a spinning anode when the tube is in rotation during a scan.

In summary, a displacement of the focal spot along the longitudinal direction is geometrically equivalent to a longitudinal displacement of the detector array. By alternating the longitudinal position of the focal spot for successive projection angles, data can be collected over two slices, in a manner similar to the dual-row detector system. However, in the present invention, only a single row of detectors and corresponding data acquisition circuits are needed to collect the same data as the hardware-intensive dual-row system.

More importantly, in the preferred configuration of FIG. 7, both fan-beam planes a,b are perpendicular to the z-axis. Consequently, the images reconstructed form this configuration are more accurate than those reconstructed from the dual-row detector system. Furthermore, unlike the dual-row detector system, the present invention offers flexibility to select the distance interval $d_i$ between the slice planes a, b. This option is consistent with applications where it is preferred to select a distance interval between the slice planes shorter than the slice width, such that the slices are partially overlapped.

Figure 12:
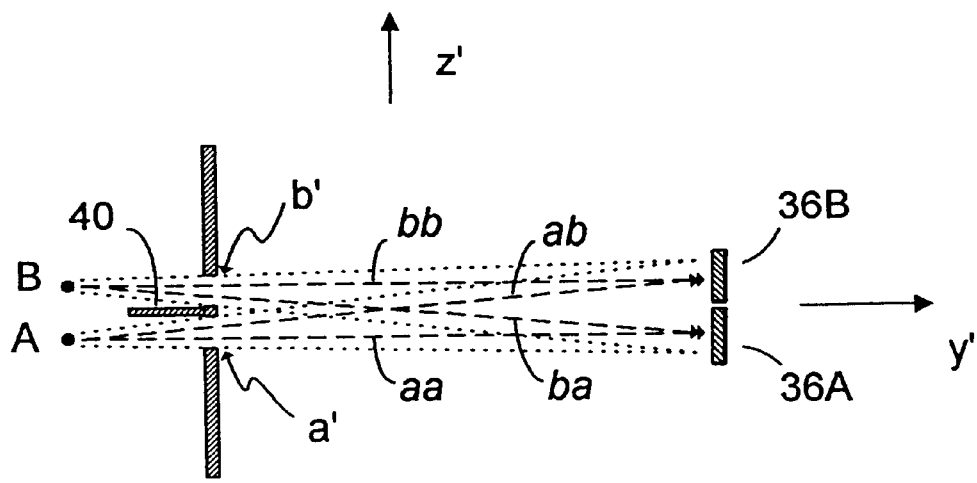
FIG 12 is a side schematic view of an alternative embodiment of the present invention illustrating the application of a longitudinal flying focal spot to a dual-row detector system, illustrating the four resulting fan-beam planes, namely aa, bb, ab, and ba.

As shown in FIG. 12, three slices can be scanned contemporaneously in this configuration with four fan-beam planes. Two of the fan-beam planes aa, bb are perpendicular to the z'-axis and data collected from these can therefore be used separately for accurate reconstruction of corresponding slices. The data collected from the two non-perpendicular fan-beam planes ab, ba can be used together to reconstruct the middle slice. The image of the middle slice may not be as uniform in slice width, nor as accurate, as the two slices reconstructed from fan beam planes aa and bb, because the fan-beam planes used for the middle slice are tilted. In any event, this configuration offers an improvement over the dual-row detector system described above with reference to FIG. 9, because at least two fan-beam planes aa, bb are parallel, and therefore well-suited for accurate reconstruction.

In existing fixed focal spot scanners, drift in the focal spot longitudinal position can occur due to a number of factors, including variance in temperature. Longitudinal focal spot drift, in turn, causes the location of incidence of the X-ray on the detectors to drift in the longitudinal direction. This is not desirable, because detector sensitivity depends, in part, on the longitudinal location. As a result of this drift, ring artifacts may appear in the image. The longitudinal drift of the focal spot is commonly measured by monitor detectors, and various techniques are used to compensate for the drift. See, for example, U.S. Pat. No. 5,550,886 issued Aug. 27, 1996 to John Dobbs and Ruvin Deych, and assigned to the present assignee.

Figure 13:
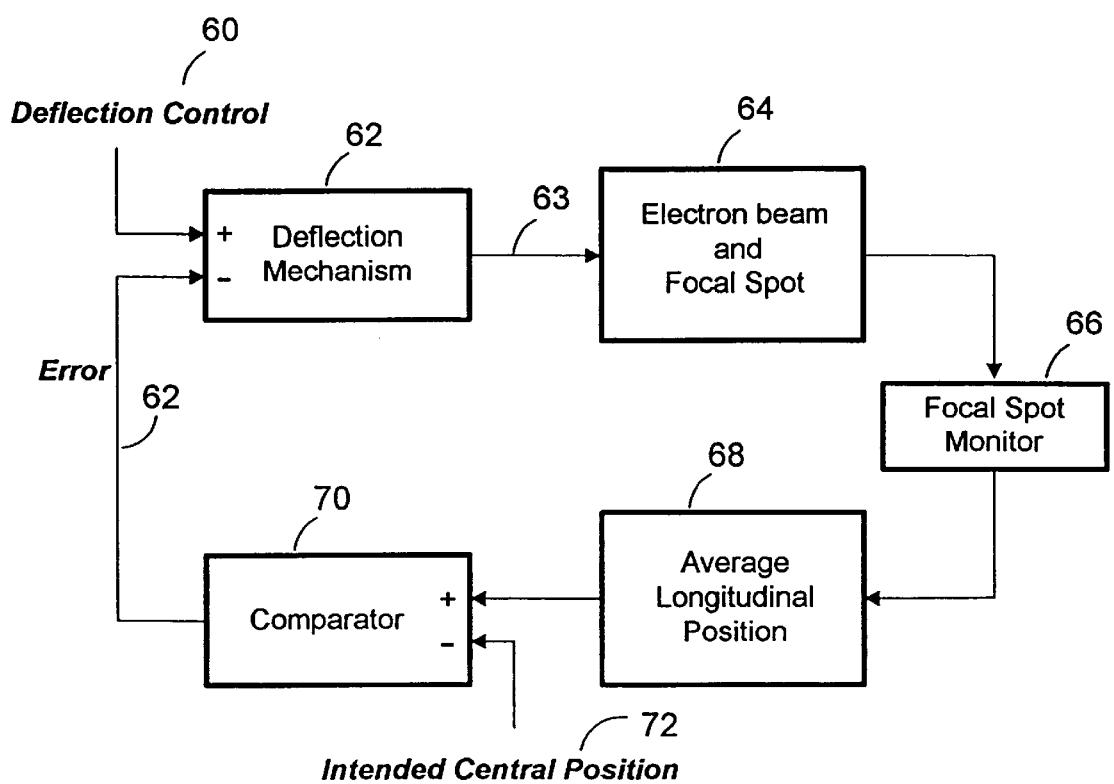
FIG. 13 is a block diagram of a system for stabilizing the longitudinal focal spot position, in accordance with the present invention.

In a preferred compensation technique in accordance with the present invention, the system using a longitudinal flying focal spot can also include a mechanism to self-correct this drift, as shown in the block diagram of FIG. 13. The focal spot position is monitored at monitor 66, and the average longitudinal position of the focal spot is determined at unit 68. The average value is compared at comparator 70 with the intended central longitudinal position 72. The difference value 74, representing the error due to drift, is fed back to the electric- or magnetic-field deflection mechanism 62 to offset the deflection control signal 60. The drift-compensated electric or magnetic field 63 deflects the electron beam and hence the focal spot 64 to the intended longitudinal positions without drifting. In this manner, the focal spot is tracked and stabilized by the feedback signal to oscillate between the same longitudinal positions.

In a preferred embodiment, the focal spot oscillates in accordance with a square waveform function with respect to time, such that the focal spot remains at desired positions A or B during sampling. However, movement in accordance with such a square waveform function is difficult to achieve. A more realistic choice would be a trapezoidal waveform function. However, for even a trapezoidal waveform function, it is difficult to achieve the required slew a rate and settling time. A more practical approach employs a sinusoidal waveform function, or similar waveform. The detecting signal is integrated or filtered over a time where the focal spot is at or near the peak of the waveform. One filter which has been found helpful in optimizing the acquired data is described in U.S. Pat. No. 5,841,829 issued Nov. 24, 1998 to Enrico Dolazza and Hans Weedon, assigned to the present assignee, and entitled Optimal Channel Filter For CT System With Wobbling Focal Spot. The integration of filtering of the detecting signal is an averaging process and is equivalent to broadening of the focal spot in the longitudinal dimension. The degree of broadening depends on the oscillating waveform and is proportional to the peak-to-peak displacement of the focal spot, which in turn is proportional to the slice interval $d_i$. For a sinusoidal waveform, the broadening is typically about one quarter of the slice interval $d_i$, and the slice width is typically equal to the slice interval $d_i$. Therefore, the degree of broadening is about one-quarter the slice width. Such a small magnitude of broadening of the focal spot in the longitudinal dimension has relatively little effect in the image. In practice, such slice-width-dependent broadening is advantageous, because it makes the thickness of the fan beams more uniform across the object. This broadening is even more beneficial for scanning of large slice widths, where the fan beams become considerably thicker toward the detector array.

In a fourth-generation CT scanner, the detector array comprising a full circle of detectors is built into the stationary gantry. The X-ray tube rotates about the object and detector array during a scan, providing successive view angles required for reconstructing the data. The longitudinal flying focal spot of the present invention is further applicable to such fourth-generation CT scanners to allow for contemporaneous scanning of at least two slices.

Existing third- or fourth-generation scanners may be upgraded for longitudinal flying focal spot scanning in accordance with the present invention. Such an upgrade may include replacement of the X-ray tube collimator. Furthermore, the data acquisition system is preferably capable of contemporaneous sampling of all detecting channels synchronized with the oscillating longitudinal position of the focal spot.

Finally, while the invention has been generally described with reference to single and dual row detection arrays, and the focal spot movable between two longitudinal positions, the detector array can include any number of rows (with one or more multiple rows being used for each desired position of the focal spot), and the slices can be acquired with the focal spot in any number of longitudinal positions.

While this invention has been particularly shown and described with references to preferred embodiments thereof, it will be understood by those skilled in the art that various changes in form and details may be made therein without departing from the spirit and scope of the invention as defined by the appended claims.

I claim:

1. A computed tomography scanner including an energy source having a focal spot and a detector array, the array including at least one row of detectors, for scanning an object at successive incremental projection angles about a longitudinal axis, said focal spot having a variable number of positions displaced in a longitudinal direction during a scan of an object so as to define at least two fan beam planes through each row of detectors, at least one of the fan beam planes being non-perpendicular to the longitudinal axis.

2. The computed tomography scanner of claim 1 wherein said focal spot is moved successively to multiple positions between corresponding successive projection angles.

3. The computed tomography scanner of claim 2 wherein said focal spot is successively moved to all of the positions substantially in accordance with an oscillating timing waveform function selected from a group consisting of square, trapezoidal, and sinusoidal waveform functions.

4. The computed tomography scanner of claim 2 wherein said focal spot successively moves between first and second peak amplitude positions in accordance with a sinusoidal waveform function, and wherein the detector array generates detector signals when the focal spot is substantially at each of the first or second peak amplitude positions.

5. The computed tomography scanner of claim 1 wherein said energy source is an X-ray source.

6. The computed tomography scanner of claim 1 wherein said detector array comprises a dual-row detector array.

7. The computed tomography scanner of claim 1 further comprising a collimator for collimating the radiation emitted from the energy source focal spot.

8. The computed tomography scanner of claim 7 wherein said focal spot successively moves between first and second positions in a longitudinal direction, and wherein the collimator further comprises:

a baffle and at least one slit for defining with said baffle two mutually exclusive apertures corresponding to said first and second positions;

wherein the baffle and said at least one opening is configured to prevent radiation emitted from a focal spot at said first position from entering said second aperture, and to prevent radiation emitted from a focal spot at said second position from entering said first aperture.

9. The computed tomography scanner of claim 1 wherein said focal spot is further variable in position along a direction lateral within a plane of rotation of the focal spot during a scan of an object.

10. The computed tomography scanner of claim 1 wherein said focal spot oscillates between first and second positions in a longitudinal direction respectively generating first and second fan beams correspondingly centered about first and second fan beam planes.

11. The computed tomography scanner of claim 10 wherein the first and second fan beam planes are substantially parallel and are incident at the detector array.

12. The computed tomography scanner of claim 11 wherein the detector array comprises first and second detector subarrays and wherein the first fan beam plane is incident at the first detector subarray and wherein the second fan beam plane is incident at the second detector subarray.

13. The computed tomography scanner of claim 10 wherein the first and second fan beam planes substantially diverge.

14. The computed tomography scanner of claim 10 wherein the first and second fan beam planes intersect between the focal spot and detector array.

15. The computed tomography scanner of claim 10 wherein the first and second fan beam planes converge at the detector array at substantially the same longitudinal position.

16. The computed tomography scanner of claim 10 wherein the detector array comprises a dual-row detector array having first and second detector subarrays, and wherein the first fan beam plane is incident at the first detector subarray, and wherein the second fan beam plane is incident at the second detector subarray, and wherein the focal spot further generates third and fourth fan beams centered about third and fourth fan beam planes, wherein the third fan-beam plane originates at the first focal post position and is incident at the second detector subarray, and wherein the fourth fan beam plane originates at the second focal spot position and is incident at the first detector subarray.

17. The computed tomography scanner of claim 1 further including a focal spot drift compensation mechanism comprising:
    a focal spot monitor for monitoring the position of said focal spot during said scan;
    an averaging unit for determining the average position of said focal spot over a time period, based on the monitored positions;
    a compensation unit for comparing the average position with a predetermined optimal position, and for modifying the focal spot position based on the comparison.

18. A method of scanning in a computed tomography scanner including an energy source having a focal spot and a detector array, including at least one row of detectors, for scanning an object at successive incremental projection angles about a longitudinal axis comprising varying the position of said focal spot in a longitudinal direction during a scan of an object so as to define at least two fan beam planes through each row of detectors, at least one of the fan beam planes being non-perpendicular to the longitudinal axis.

19. The method of claim 18 further comprising moving the focal spot successively to multiple positions in the longitudinal direction at each successive projection angle.

20. The method of claim 19 wherein the focal spot is successively moved to all of the positions substantially in accordance with an oscillatory timing waveform function selected from the group consisting of square, trapezoidal, and sinusoidal waveform functions.

21. The method of claim 19 further comprising moving said focal spot between first and second peak amplitude positions in accordance with a sinusoidal waveform function, and wherein the detector array generates detector signals when the focal spot is substantially at each of the first and second peak amplitude positions.

22. The method of claim 18 wherein said energy source is an X-ray source.

23. The method of claim 18 wherein said detector array comprises a dual-row detector array.

24. The method of claim 18 further comprising collimating the radiation emitted from the energy source focal spot.

25. The method of claim 24 wherein said focal spot successively moves between first and second positions in a longitudinal direction and wherein the collimator further comprises:
    first and second apertures corresponding with said first and second positions; and
    a baffle configured to prevent radiation emitted from a focal spot at said first position from entering said second aperture, and to prevent radiation emitted from a focal spot at said second position from entering said first aperture.

26. The method of claim 18 wherein said focal spot further varies in position along a lateral direction within a plane of rotation of the focal spot during a scan of an object.

27. The method of claim 18 further comprising oscillating said focal spot between first and second positions in a longitudinal direction generating first and second fan beams correspondingly centered about first and second fan beam planes.

28. The method of claim 27 wherein the first and second fan beam planes are substantially parallel and are incident at the detector array.

29. The method of claim 28 wherein the detector array comprises first and second detector subarrays, each sub array including at least one row of detectors, and wherein the first fan beam plane is incident at the first detector subarray and wherein the second fan beam plane is incident at the second detector subarray.

30. The method of claim 27 wherein the first and second fan beam planes substantially diverge.

31. The method of claim 27 wherein the first and second fan beam planes intersect between the focal spot and detector array.

32. The method of claim 27 wherein the first and second fan beam planes converge at the detector array at substantially the same longitudinal position.

33. The method of claim 27 wherein the detector array comprises a dual-row detector array having first and second detector subarrays, and wherein the first fan beam plane is incident at the first detector sub array, and wherein the second fan beam plane is incident at the second detector subarray, and wherein the focal spot further generates third and fourth fan beams centered about third and fourth fan beam planes, wherein the third fan-beam plane originates at the first focal post position and is incident at the second detector subarray, and wherein the fourth fan beam plane originates at the second focal spot position and is incident at the first detector subarray.

34. The method of claim 18 further comprising:
    monitoring the position of said focal spot during said scan;

determining the average position of said focal spot over a time period, based on the monitored positions;

comparing the average position with a predetermined optimal position, and for modifying the focal spot position based on the comparison.

35. A method of contemporaneously forming at least two 2D CT slices displaced from one another along the rotation axis of the scanner having a X-ray source defining a focal spot and at least one row of detectors, comprising moving the focal spot in an oscillatory motion between at least two points displaced from one another in a direction parallel to the rotation axis so as to define at least two fan beam planes through each row of detectors, at least one of the fan beam planes being no-Mperpendicular to the longitudinal axis such that the CT slices are generated from data acquired by projecting X-rays in the fan beam planes.

* * * * *

UNITED STATES PATENT AND TRADEMARK OFFICE
CERTIFICATE OF CORRECTION

PATENT NO.    : 6,256,369 B1
DATED         : July 3, 2001
INVENTOR(S)   : Ching-Ming Lai It is certified that error appears in the above-identified patent and that said Letters Patent is hereby corrected as shown below:

<u>Column 12,</u>
Line 56, delete "sub array", and insert therefor -- subarray --;

<u>Column 14,</u>
Line 6, delete "no-Mperpendicular", and insert therefor -- non-perpendicular --.

Signed and Sealed this

Seventh Day of May, 2002

Attest:

JAMES E. ROGAN
*Attesting Officer*  *Director of the United States Patent and Trademark Office*